United States Patent [19]

Goeb

[11] 3,996,295
[45] Dec. 7, 1976

[54] PREPARATION OF DIMETHYLSULFOXIDE BY LIQUID PHASE REACTION OF DIMETHYSULFIDE AND HYDROGEN PEROXIDE

[75] Inventor: André Goeb, Capvern les Bains, France

[73] Assignee: Produits Chimiques Ugine Kuhlmann, Paris, France

[22] Filed: July 7, 1975

[21] Appl. No.: 593,370

[30] Foreign Application Priority Data

July 4, 1974 France .............................. 74.23264

[52] U.S. Cl. .......................................... 260/607 D
[51] Int. Cl.² ....................................... C07C 147/14
[58] Field of Search ................. 260/607 D, 607 O X

[56] References Cited

UNITED STATES PATENTS 3,708,542   1/1973   Douchet et al. ............... 260/607 D
3,792,095   2/1974   Burmistrova ............. 260/607 O X

*Primary Examiner*—Lewis Gotts
*Assistant Examiner*—D. R. Phillips
*Attorney, Agent, or Firm*—Pennie & Edmonds

[57] ABSTRACT

Dimethylsulfoxide is prepared by a method which comprises adding separately dimethylsulfide and an aqueous solution of about 30 to 60 percent by weight hydrogen peroxide to a stirred aqueous liquid reaction medium under an atmosphere of inert gas, said reaction medium containing sufficient dimethylsulfoxide to solubilize the dimethylsulfide.

Dimethylsulfoxide has many known uses, particularly as a solvent in spinning polymers, extracting hydrocarbons and the like.

11 Claims, No Drawings

PREPARATION OF DIMETHYLSULFOXIDE BY LIQUID PHASE REACTION OF DIMETHYSULFIDE AND HYDROGEN PEROXIDE

BACKGROUND OF THE INVENTION

The present invention provides a procedure for manufacture of dimethylsulfoxide by oxidation of dimethylsulfide by means of hydrogen peroxide.

Several methods have been proposed to accomplish the oxidation of organic sulfides to corresponding sulfoxides. Industrially, for example, dimethylsulfoxide is made by oxidizing of dimethylsulfide with oxygen in the presence of nitrogen dioxide (Kirk-Othmer, Encyclopedia of Chemical Technology, 3d Ed., Vol. 19, pages 332 and 333). This procedure involves a number of deficiencies, however. It is specially dangerous in that mixtures of dimethylsulfide and oxygen are explosive over a wide range of composition. It is difficult to stop the oxidation at the dimethylsulfoxide level and greater than negligible quantities of dimethylsulfone are formed which must subsequently be separated. Furthermore, the crude dimethylsulfoxide is very acid and must be neutralized before being dried and distilled.

Other agents for oxidizing dimethylsulfide indicated in the literature include hydrogen peroxide, ozone and organic hydroperoxides.

In regard to oxidation by hydrogen peroxide, the prior procedures involve various disadvantages such as the necessity to work at low temperature and to use special apparatus, the critical dependence on pH and, above all, the obtainment of a dimethylsulfoxide containing more than its weight of water.

Russian patent No. 165,713, for example, describes the oxidation of dimethylsulfide by 30 percent hydrogen peroxide by bubbling dimethylsulfide vapor mixed with a gas, such as air, through the peroxide solution at 50° C. in an apparatus having five oxidation columns.

In Russian patent No. 175,055 the dimethylsulfide is preliminarily treated with sufficient cuprammonium solution to obtain a pH $\geq$ 8, and then is mixed under very rapid agitation (6000 rpm) with 30 percent aqueous hydrogen peroxide at a temperature not exceeding 20° C.

In Russian patent No. 249,375 dimethylsulfide is treated with sulfuric acid until the concentration of sulfur dioxide in dimethylsulfide reaches 4 to 11 grams/liter, before then oxidizing with 30 percent aqueous hydrogen peroxide.

SUMMARY OF THE INVENTION

A method has now been found whereby dimethylsulfoxide is prepared by oxidation of dimethylsulfide with hydrogen peroxide under safe conditions which avoid the above-mentioned difficulties and achieve unexpectedly high yields.

Briefly stated, the present invention provides a method of preparing dimethylsulfoxide which comprises adding separately dimethylsulfide and an aqueous solution of about 30 to 60 percent by weight hydrogen peroxide to a stirred aqueous liquid reaction medium under an atmosphere of inert gas, said reaction medium containing sufficient dimethylsulfoxide to solubilize the dimethylsulfide.

DETAILED DESCRIPTION

The instant method is characterized by the fact that oxidation of dimethylsulfide by hydrogen peroxide is carried out in an aqueous starting solution of dimethylsulfoxide without using any supplementary reagents.

An advantage of this method is that the working conditions are safe. Furthermore, the hydrogen peroxide is more concentrated than that used in prior art, resulting in a less diluted dimethylsulfoxide. A further advantage is that the crude dimethylsulfoxide obtained can be easily improved or purified by subjecting the produce leaving the oxidation reactor to a washing with dimethylsulfide.

According to the procedure of the present invention, dimethylsulfide and hydrogen peroxide are made to react in liquid phase, the dimethylsulfide and hydrogen peroxide being introduced separately into a reaction medium comprising dimethysulfoxide in aqueous solution. Although hydrogen peroxide and dimethylsulfide are only weakly soluble in each other, it has been established by the present applicant that in using the aqueous dimethylsulfoxide as the reaction medium, dimethylsulfide is sufficiently soluble therein to assure a rapid reaction. The starting solution of aqueous dimethylsulfoxide is conveniently provided by saving a fraction or "heel" of the crude aqueous dimethylsulfoxide prepared in a preceding manufacturing batch.

The temperature of the reaction can vary over considerably wide limits. Care must be taken, however, to maintain the dimethylsulfide in solution, which implies working at a superatmospheric pressure if the chosen reaction temperature is higher than the boiling temperature of the dimethylsulfide - water - dimethylsulfoxide system of the reaction medium. It is preferable to maintain the temperature between about 30° and 40° C. which permits using water as a cooling means and avoids the need of using elevated pressure. It is advantageous and practical to work either at atmospheric pressure or under slight overpressure, the latter serving to prevent evaporation losses. Furthermore, there is no incentive to increase temperature since this would risk stronger oxidation, with in particular the formation of sulfone.

The concentration of hydrogen peroxide used in the method of this invention can vary over wide limits. The concentration by weight can be between about 30 percent and 60 percent. It is, however, not desirable to use too high a concentration because it is then more difficult to obtain conversion of all the hydrogen peroxide in a reasonable period of time. On the other hand, it is not desirable to use a hydrogen peroxide as dilute as in prior methods, because productivity is then diminished, and furthermore a considerably increased amount of energy is later required to dehydrate the dimethylsulfoxide. In one of the preferred embodiments of this invention, the concentration of hydrogen peroxide used is between about 35 and 55 percent, the optimum choice being dependent on the local economic conditions. This leads to the production of a crude dimethylsulfoxide of concentration between about 50 and 65 percent by weight.

In order to form a mol of dimethysulfoxide according to the reaction $CH_3-S-CH_3 + H_2O_2 \rightarrow CH_3-SO-CH_3 + H_2O$, it is necessary to react one mol of hydrogen peroxide per mol of dimethylsulfide.

It is advantageous, however, to work with a small excess of dimethylsulfide over the amount required for stoichiometric equivalence in order to convert the hydrogen peroxide completely. A molar ratio of dimethylsulfide to hydrogen peroxide between about 1.05/1 and 1.25/1 is favorable. The excess of dimethylsulfide does not give rise to any particular difficulties since a large part of that excess is soluble in the reaction medium so that the reaction proceeds practically under the conditions of homogeneous phase. Furthermore, it is relatively easy to eliminate the excess dimethylsulfide from the crude dimethylsulfoxide end-product by stripping, either by sparging with an inert gas like nitrogen, or by distilling. The recovered dimethylsulfide can then be recycled.

When the molar ratio of dimethylsulfide to hydrogen peroxide is greater than 1.1, a dimethylsulfide liquid phase, immiscible in the dimethylsulfoxide, separates out on cooling. Any small amounts of sulfur-containing by-product impurities, such as disulfides, are preferentially soluble in this separated dimethylsulfide, which thus acts simultaneously as an extraction agent for the impurities from the dimethylsulfoxide.

The concentration of the dimethylsulfoxide in the aqueous reaction medium can vary within fairly wide limits and will generally depend upon the concentration of hydrogen peroxide being reacted. The amount of dimethylsulfoxide should be sufficient to insure substantially complete solubilization of the dimethylsulfide at the reaction temperature so that the dimethylsulfide and the hydrogen peroxide are made to react in liquid phase. For most reactions, such as those disclosed herein in the Example, the aqueous reaction medium can contain about 44 to 66 percent by weight dimethylsulfoxide.

It is also possible to improve the extraction of impurities by supplying a supplementary charge of dimethylsulfide and interposing a liquid-liquid extraction step. But such augmentation is generally not necessary to take care of what are usually only trace quantities of impurities formed in the procedure of this invention.

After separation therefrom of the high-boiling impurities, for example by distillation, the recovered dimethylsulfide can be placed anew into the reaction.

The reaction can be carried out without difficulty discontinuously or continuously or in any intermediate form which one skilled in the art might desire. In all cases, the oxidation reactor is equipped with sufficient agitation to facilitate the homogeneous contact between the reactants, the dissolution of dimethylsulfide and the dilution of the hydrogen peroxide; with means for separate introduction of the two reactants into the reaction medium; and efficient cooling means capable of eliminating the heat of reaction. For reasons of safety, it is recommended to carry out the operation under an atmosphere of inert gas.

The operation can be carried out discontinuously in a single oxidation reactor and high yield of the dimethylsulfoxide can be attained in such manner. In the other cases, in spite of the high rate of reaction, however, it is preferable to carry out the oxidation in several reactors in cascade arrangement. By way of example, a series of two reactors can be used wherein the oxidation in the first reactor is carried out to the point of at least 90 percent conversion of the hydrogen peroxide; then the product is passed on to a second or finishing reactor designed to effect an efficient completion of the conversion.

Oxidation of dimethylsulfide by the method of this invention produces a dimethylsulfoxide of excellent quality. After eliminating the excess dimethylsulfide, the aqueous crude dimethylsulfoxide is always practically colorless and generally contains less than 1 percent by weight of organic sulfur containing impurities.

The preparation of pure anhydrous dimethylsulfoxide from this crude is carried out according to the known art without particular difficulties.

A further advantage of the method of this invention is its complete safety under the described working conditions, the oxygen content of the gaseous atmosphere of the reactor never exceeding 0.5 percent.

The introduction of traces of alkali to modify the pH of the reaction medium and/or stabilizers can be added but such is usually superflous by virtue of the selectivity and high yields obtained by this method.

The invention will be further illustrated by description in connection with the following specific examples wherein, as also elsewhere herein, proportions are by weight unless otherwise stated.

EXAMPLE 1

Into a reactor of 200 cm.$^3$ size, equipped with agitation, under a blanket of nitrogen and with temperature maintained at 35° C., 129 grams of an aqueous solution containing 48.5 percent by weight dimethylsulfoxide is charged, followed by 20 grams of 34 percent (by weight) hydrogen peroxide. A trace of ammonia is added sufficient to raise the apparent pH of the solution to 9.

There is then introduced in a uniform manner over a period of 8 minutes, 18.6 grams of dimethysulfide. The reaction medium is analyzed to follow the consumption of hydrogen peroxide. Fifteen minutes after the start of dimethylsulfide addition, the residual hydrogen peroxide is 15 millimoles. After about one hour of reaction, less than 0.2 millimoles remain, corresponding to a fraction of hydrogen peroxide conversion greater than 99 percent.

EXAMPLE 2

Into a reactor of 350 cm.$^3$ equipped as the reactor in the preceding example, there is charged 169 grams of 64.5 percent by weight solution of dimethylsulfoxide in water, then 20.4 grams of an aqueous solution containing 58 percent by weight of hydrogen peroxide. The temperature of the reactor is maintained at 35° C during the entire experiment. The apparent pH of the reaction medium is 4.1–4.2. Over a period of seven minutes, 32.6 grams of dimethylsulfide is added. The apparent pH of the reaction medium does not change and remains at 4.2. The gaseous atmosphere of the reactor is analyzed by means of a SERVOMEX analyzer for oxygen; the concentration of oxygen remains less than 0.2 percent during the entire operation. The consumption of hydrogen peroxide is followed as a function of time. After 30 minutes of reaction, 82 millimoles of $H_2O_2$ remain. After 2 hours of reaction, the conversion of $H_2O_2$ reaches 95 percent. After 3 hours the conversion is 97 percent. This example shows that while some of the benefits of this invention are obtained at such extremely high concentration of $H_2O_2$, it is nevertheless less preferable to use such high concentration if it is desired to obtain a high conversion of $H_2O_2$ in a reasonable length of time.

EXAMPLE 3

An installation for the production of dimethylsulfoxide functioning continuously comprises a first reactor of the KELLER type, size 200 cm.$^3$ and equipped with agitation, cooling means comprising a submerged coil and two inlet pipes, one for hydrogen peroxide and the other for dimethylsulfide. This reactor is maintained under a blanket of nitrogen and functions at a constant level. The product leaving the first reactor is supplied to a second reactor comprising a coil having internal diameter 10 millimeters, submerged in a thermostat bath. The product which has passed through this finishing reactor then is fed continuously to the top of a stripping column to be freed of the excess dimethylsulfide.

The temperature is maintained at 35° C. in the two reactors. The first reactor containing 50 grams of an aqueous starting solution of 54 percent by weight dimethylsulfoxide is fed continuously with a stream of dimethylsulfide at a rate of 1.10 mols per hour and another stream of 44 percent aqueous solution of hydrogen peroxide at a rate of 1.0 mols/hours. The apparent pH of the first reactor is maintained at 8.8–9 by addition of traces of ammonia. The volumes of the contents of the two reactors are regulated in such a manner that the average time of sojourn reaches 65 minutes in the first reactor and 60 minutes in the second. The analysis of the product leaving the two reactors shows a 91 percent conversion of hydrogen peroxide at the exit of the first reactor and a 99 percent conversion at the exit of the second reactor. The oxygen content of the gas superimposed on the reaction medium in the first reactor remains less than 0.2 percent throughout the entire run. The crude aqueous product leaving the bottom of the stripping column contains 53.6–54 percent by weight dimethylsulfoxide and is clear and practically colorless, having a coloration of the American Public Health Association scale of less than 5.0.

EXAMPLE 4

A similar installation operating in continuous sequence uses a first reactor of 350 ml. equipped as the first reactor of Example 3, with the exception of the continuous efflux. In this reactor, filled at the start with a 54 percent by weight aqueous solution of dimethylsulfoxide to half its volume, there is introduced continuously over a period of 20 minutes, 1.2 mols of dimethylsulfide, then staggered by 5 minutes, in the same manner, 1 mol of 41.8 percent by weight aqueous solution of hydrogen peroxide. At the end of these additions, i.e., 25 minutes after the start of the cycle, the reactor is at its maximum level. The reaction is allowed to continue, the temperature being maintained at 35° C. and the apparent pH of the solution is 4.1–4.3. At 55 minutes after the start of the cycle, about half of the contents are drained out from the reactor into a second reactor, also maintained at 35° C. Analysis of the medium made just before this draining operation shows a hydrogen peroxide content approximately equal to 0.005 mols per 100 grams, corresponding to a conversion of $H_2O_2$ equal to about 98.3 percent. At the end of 60 minutes a new cycle is started. The product collected in the second reactor is kept there for 30 minutes at 35° C., then transferred to a vessel which supplies continuously a stripping column, and which is kept at 20° C. so as to permit decantation of a part of the dimethylsulfide. This dimethylsulfide is lightly colored and shows the presence of small quantities of dimethyldisulfide and ethylmethyldisulfide which are absent from the crude dimethylsulfoxide produced.

After continuous passage over the stripping column, an aqueous product is obtained which is found by analysis to contain about 54 percent by weight of dimethylsulfoxide, containing less than 0.5 grams/liter of dimethylsulfone, and having an acid number equal to 0.030 milligrams KOH per gram. In addition, the analysis shows that consumption of $H_2O_2$ has been complete. In summary, in this experiment there has been obtained a practically complete conversion of hydrogen peroxide with a very small amount of by-products.

What I claim is:

1. A method of forming dimethylsulfoxide which comprises:
   introducing dimethylsulfide and hydrogen peroxide into a substantially homogeneous aqueous-dimethylsulfoxide liquid reaction medium wherein the dimethylsulfide is introduced in amounts soluble in the reaction medium and the dimethylsulfoxide is present in the reaction medium in amounts of from about 44 percent to 66 percent by weight;
   mixing the dimethylsulfide and the hydrogen peroxide in the liquid medium for a time sufficient to cause oxidation of the dimethylsulfide and substantially complete conversion of the hydrogen peroxide; and
   recovering the dimethylsulfoxide formed.

2. The method of claim 1, wherein the mol ratio of dimethylsulfide to hydrogen peroxide used is between about 1.5/1 and 1.25/1.

3. The method of claim 2 in which the dimethylsulfide and hydrogen peroxide are separately added to the reaction medium and the hydrogen peroxide is an aqueous solution containing about 30 to 60 percent by weight hydrogen peroxide.

4. The method of claim 3, wherein the reaction medium is maintained at a temperature of about 30° to 40° C.

5. The method of claim 3, wherein the added aqueous solution of hydrogen peroxide contains about 35 to 55 percent by weight hydrogen peroxide.

6. The method of claim 2 wherein the reaction is carried out under a gaseous atmosphere in which the oxygen content does not exceed about 0.5 percent.

7. The method of claim 3, wherein the reaction medium is a fraction of the crude reaction product obtained by previously carrying out the method of claim 1.

8. The method of claim 3, wherein the crude dimethylsulfoxide obtained is purified by washing with dimethylsulfide.

9. The method of claim 6, wherein the added aqueous solution of hydrogen peroxide contains about 35 to 55 percent by weight hydrogen peroxide.

10. The method of claim 6, wherein the reaction medium is a fraction of the crude reaction product obtained by previously carrying out the method of claim 1.

11. The method of claim 6, wherein the crude dimethylsulfoxide obtained is purified by washing with dimethylsulfide.

* * * * *

UNITED STATES PATENT AND TRADEMARK OFFICE
CERTIFICATE OF CORRECTION

PATENT NO. : 3,996,295
DATED : December 7, 1976
INVENTOR(S) : André Goeb

It is certified that error appears in the above-identified patent and that said Letters Patent are hereby corrected as shown below:

Column 1, Line 21, "guantities" should read --quantities--

Column 2, Line 9, "produce" should read --product--

Column 3, Line 27, "Example" should read --Examples--

Column 4, Line 27, "dimethysulfide" should read --dimethylsulfide--

In the Title, "DIMETHYSULFIDE" should read --DIMETHYLSULFIDE--

Signed and Sealed this

Twelfth Day of April 1977

[SEAL]

Attest:

RUTH C. MASON
*Attesting Officer*

C. MARSHALL DANN
*Commissioner of Patents and Trademarks*